United States Patent [19]

Shimizu et al.

[11] Patent Number: 5,024,942

[45] Date of Patent: Jun. 18, 1991

[54] BIOCHEMICAL PROCESS FOR REACTING HYDROPHOBIC AND HYDROPHILIC SUBSTRATES AND APPARATUS THEREFOR

[75] Inventors: Shoichi Shimizu; Tsuneo Yamane, both of Aichi, Japan

[73] Assignee: Nippon Oil and Fats Co., Ltd., Tokyo, Japan

[21] Appl. No.: 581,018

[22] Filed: Feb. 17, 1984

[30] Foreign Application Priority Data

Feb. 21, 1983 [JP] Japan .................................. 58-28325

[51] Int. Cl.⁵ ........................... C12P 7/64; C12P 7/62; C12M 1/40
[52] U.S. Cl. .................................. 435/134; 435/135; 435/161; 435/162; 435/174; 435/177; 435/180; 435/198; 435/288
[58] Field of Search ............... 435/161, 162, 288, 311, 435/134, 135, 177, 174, 180, 198

[56] References Cited

U.S. PATENT DOCUMENTS 4,275,081 6/1981 Coleman et al. ...................... 426/33

FOREIGN PATENT DOCUMENTS 57-166985 10/1982 Japan .................................. 435/288

OTHER PUBLICATIONS

Kirk-Othmer, Encyclopedia of Chemical Technology, Third Ed., vol. 5, John Wiley & Sons, Inc., New York, pp. 62-69, (1979).
Kirk-Othmer, *Encyclopedia of Chemical Technology*, vol. 8, p. 196, (1965).

*Primary Examiner*—Elizabeth C. Weimar
*Assistant Examiner*—Gail Poulos
*Attorney, Agent, or Firm*—Sughrue, Mion, Zinn, Macpeak & Seas

[57] ABSTRACT

A biochemical process and apparatus for use in the process are described. The process comprises reacting (a) a hydrophobic substrate with (b) a solution or dispersion comprising a hydrophilic substrate and an enzyme catalyst, by contacting through a porous thin membrane, wherein the hydrophobic and hydrophilic substrates are incompatible with each other. The apparatus comprises a main body and a porous thin membrane provided inside the main body so as to define therein at least two channels, wherein a hydrophobic substrate and a solution or dispersion comprising hydrophilic substrate and an enzyme catalyst are contacted through the thin membrane by passing them through the respective channels.

8 Claims, 1 Drawing Sheet

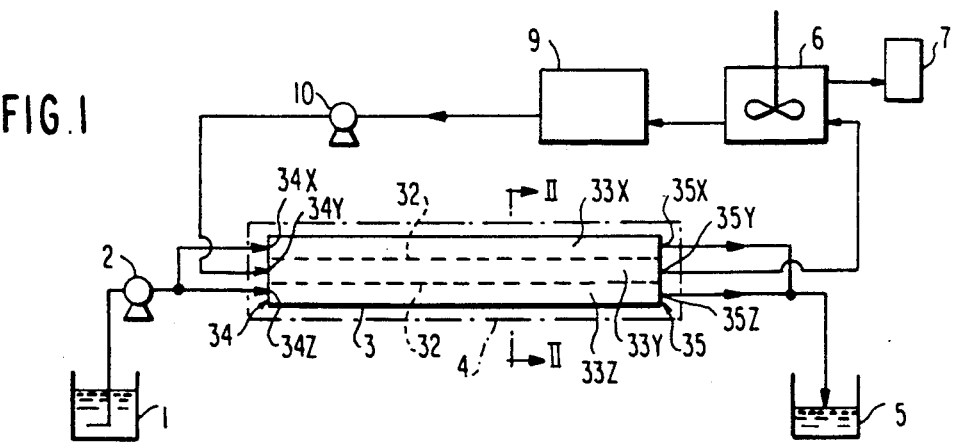
FIG.1
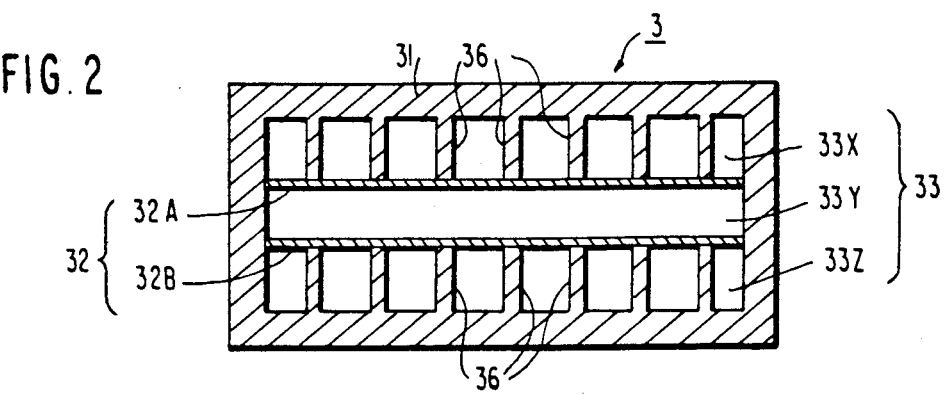
FIG.2
FIG.3A
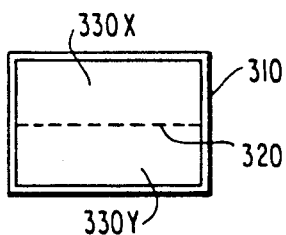
FIG.3B
FIG.3C
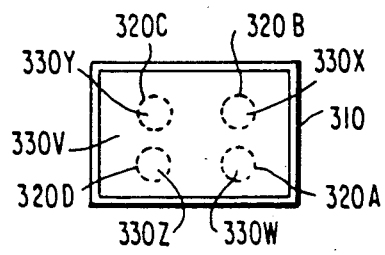
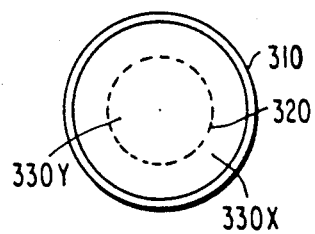
FIG.3D

BIOCHEMICAL PROCESS FOR REACTING HYDROPHOBIC AND HYDROPHILIC SUBSTRATES AND APPARATUS THEREFOR

FIELD OF THE INVENTION

The present invention relates to a biochemical process which allows hydrophobic and hydrophilic substrates, which are incompatible with each other, to react with high efficiency without mixing them, and an apparatus for use in the process.

BACKGROUND OF THE INVENTION

Biochemical reactions utilizing enzymes as a catalyst, such as (a) the hydrolysis of hydrophobic fats and oils, and (b) the esterification of hydrophobic higher fatty acids and hydrophilic polyhydric alcohols, have heretofore been performed by immobilizing the enzymes, or by dissolving or dispersing the enzymes in a hydrophilic substrate and completely mixing together the hydrophobic and hydrophilic substrates which are incompatible with each other.

In the latter process wherein the enzymes are not immobilized, the hydrophobic and hydrophilic substrates are converted into an emulsion when completely mixed together since the enzymes also act as surface active agents. When heated to temperatures of at least about 80° C. after the reaction is completed, the emulsion separates into two layers. At such a temperature, the enzymes are inactivated, and the thus-inactivated enzymes enter the hydrophobic layer.

In the case of the above-described hydrolysis of fats and oils, even if the emulsion separates into two layers, part of the glycerol produced, which is a hydrolyzate, enters and mixes with the hydrophobic higher fatty acid layer. Similarly, in the case of the esterification of hydrophobic higher fatty acids and hydrophilic polyhydric alcohols, the product, i.e., a hydrophobic ester layer, is contaminated with part of the unreacted polyhydric alcohol. From an economic standpoint, the inactivation of expensive enzymes is a particular serious disadvantage of the mixing process.

In order to overcome the above-described problems of the latter process, the former process as described above, was developed, i.e., wherein immobilized enzymes are used and the enzymes can be recovered. However, this process has disadvantages in that the cost of immobilization is high and the enzyme activity is low. In addition, the heterogeneous reaction cannot be performed efficiently. Thus, the process utilizing immobilized enzymes has not been put into practical use.

SUMMARY OF THE INVENTION

An object of the present invention is to provide a biochemical process for reacting hydrophobic substrates with hydrophilic substrates, wherein the enzyme catalyst is not immobilized and is easily recoverable.

Another object of the present invention is to provide a biochemical process for reacting hydrophobic substrates with hydrophilic substrates, wherein the enzyme catalyst is not deactivated.

A further object of the present invention is to provide a biochemical process for reacting hydrophobic substrates with hydrophilic substrates, wherein the hydrophobic and hydrophilic substrates are not intermixed.

A still further object of the present invention is to provide a biochemical process for reacting hydrophobic substrates with hydrophilic substrates, wherein the reaction products are not contaminated with the substrates and are easily recoverable.

The present invention meets the above-described objects and provides a biochemical process which is completely different from the conventional processes. In addition, the present invention provides an apparatus for use in the process.

Specifically, in one embodiment, the present invention relates to: a biochemical process comprising reacting (a) a hydrophobic substrate with (b) a solution or dispersion comprising a hydrophilic substrate and an enzyme catalyst, by contacting said hydrophilic and said hydrophobic substrates through a porous thin membrane, wherein said hydrophilic and hydrophobic substrates are incompatible with each other.

In another embodiment, the present invention relates to an apparatus for use with said biochemical process comprising:

a main body; and a porous thin membrane placed in the main body so as to define at least two channels, each channel being provided with an inlet and an outlet, wherein a hydrophilic substrate and a hydrophobic substrate, which are incompatible with each other, can be introduced separately into different channels through the inlets provided therefor and reacted with a solution or dispersion comprising the hydrophilic substrate and an enzyme catalyst, by contacting the substrates through the porous thin membrane, while at the same time the hydrophobic reaction product and the hydrophilic reaction product containing the enzyme and surplus hydrophilic substrate can be withdrawn through the outlets provided therefor.

BRIEF DESCRIPTION OF THE DRAWINGS

FIG. 1 is a flow diagram of a system including the apparatus of the present invention.

FIG. 2 is a cross-sectional view taken along line II—II of FIG. 1.

FIGS. 3(A) to 3(D) are front views of other embodiments of the apparatus of the present invention. 31, 310 represent the main body. 32 (32A, 32B), 320 (320A, 320B, 320C, 320D) represent the porous thin membrane. 33 (33X, 33Y, 33Z), 330 (330V, 330W, 330X, 330Y, 330Z) represent channels. 34 (34X, 34Y, 34Z) represents inlets. 35 (35X, 35Y, 35Z) represents outlets.

DETAILED DESCRIPTION OF THE INVENTION

The hydrophobic and hydrophilic substrates which are incompatible with each other are defined as follows. In the hydrolysis of fatty acid esters such as fats and oils, the fats and oils and other fatty acid esters are the hydrophobic substrates and water is the hydrophilic substrate. In the synthesis of fatty acid/polyhydric alcohol esters, fatty acids having from 6 to 24 carbon atoms, particularly higher fatty acids, are the hydrophobic substrates and polyhydric alcohols such as ethylene glycol, propylene glycol and glycerol are the hydrophilic substrates. In the synthesis of higher fatty acid/-polyhydric alcohol partial esters through an ester exchange reaction of fats and oils and polyhydric alcohols, fats and oils are the hydrophobic substrates and the polyhydric alcohols are the hydrophilic substrates.

Enzymes which can be used in the present invention are generally known as lipases and include lipases produced by microorganisms belonging to the genera Candida, Chromobacterium, Aspergillus, Penicillium, Mucor, Geotrichum, Rhizopus, and Arthrobacter; lipases produced by animal organs such as the pancreas; and lipases obtained from plant seeds such as castor beans. When these lipases are used, they are powered and dissolved or dispersed in the hydrophilic substrate. In addition, a broth or broth without microorganisms, containing lipases can be used.

Porous thin membranes which can be used in the present invention may be made of either inorganic materials such as glass and metals, or organic materials such as synthetic resins. The pore size generally ranges between 0.05 and 10 $\mu$m. It is convenient to use commercially available membrane filters for microfiltration. These membrane filters may be made of either hydrophilic materials such as cellulose acetate or hydrophobic materials such as polytetrafluoro ehtylene and polypropylene. The thickness of the porous thin membranes is generally from 10 to 100 $\mu$m, preferably from 20 to 50 $\mu$m. The porosity of the porous thin membranes is generally from 20 to 80%, preferably from 40 to 60%.

If the pore size is less than 0.05 $\mu$m, the reaction rate is small, whereas if it is greater than 10 $\mu$m, the two substrates undesirably mix with each other. It is desirable for the thickness and porosity of the thin membranes to be adjusted within the above-described ranges from the viewpoint of the reaction rate and the practical strength of the thin membranes.

The two substrates which are incompatible with each other are contacted through a porous thin membrane as described above until the reaction reaches a predetermined stage. The two substrates are separated from each other by the thin membrane and will not intermingle. The substrates are allowed to react upon contact through the micropores of the thin membrane.

The reaction temperature is determined by the temperature dependency of the reaction rate and the heat stability of the enzymes which will vary with the type thereof employed. As the temperature is raised, the viscosity of the substrates such as fats and oils, fatty acids, and polyhydric alcohols, drops and the reaction rate increases. Thus, elevated temperatures are preferred. However, as the temperature is raised, the enzymes are more easily inactivated. Thus, from the viewpoint of stability, low temperatures are preferred. In general, it is efficient to perform the process of the present invention at as high a temperature as possible within the range within which the lipases are not inactivated.

In the hydrolysis of fats and oils, if the fats and oils are solid, the reaction temperature is preferably at least 10° C. higher than the melting point thereof in view of the convenience of pumping. In general, the reaction is carried out at about 40° C. for marine oil and vegetable oil which are liquid at room temperature, and at about 50°-60° C. for solid fats and oils such as tallow, lard and palm oil. The lipases are used in the form of aqueous solutions or may in part, be employed in a dispersion.

The esterification of higher fatty acids and polyhydric alcohols is performed at a temperature ranging between about 40°-60° C. for the same reasons as described above. In this esterification, the lipases are dissolved or dispersed in the polyhydric alcohols. The water content of the polyhydric alcohols is sufficient to be not more than 10% by weight and is preferably from 2 to 5% by weight.

With regard to the reaction products, the hydrophilic reaction products are transferred to the hydrophilic substrate, and the hydrophobic reaction products are transferred to the hydrophobic substrate. The enzymes remain dissolved in the hydrophilic substrate. Therefore, the desired reaction product is easy to separate and recover, and the enzymes can be easily recovered and reused. The reaction products are generally hydrophobic higher fatty acids for the hydrolysis of fats and oils, and hydrophobic fatty acid esters for the esterification of hydrophobic higher fatty acids and hydrophilic polyhydric alcohols.

The apparatus of the present invention will hereinafter be explained with reference to the esterification of a higher fatty acid and glycerol using lipase as a catalyst.

FIG. 1 shows a flow diagram of a system including the apparatus of the present invention. This system comprises a higher fatty acid reservoir 1, a lipase-containing glycerol reservoir 9, pumps 2 and 10, a rectangular parallelopiped reaction unit 3, a thermostatic bath 4, a reservoir 5 where the desired hydrophobic reaction product, i.e. fatty acid glyceride is to be stored, a reservoir 6 where a mixture of lipase, glycerol, water and one of the reaction products is to be stored, and a vacuum pump 7.

Reaction unit 3 comprises, as illustrated in FIG. 2, a main body 31 made of plastic and rectangular in cross-section. Two porous thin flat shaped membranes 32A and 32B are provided in the main body 31; three channels 33X, 33Y and 33Z are defined in the inside of the main body 31 by the two thin membranes 32A and 32B; feedstock-introduction inlets 34X, 34Y and 34Z are provided at one end of channels 33X, 33Y and 33Z, respectively; reaction product-withdrawal outlets 35X, 35Y and 35Z are provided at the other end of channels 33X, 33Y and 33Z; and a plurality of bank-like projections are formed integrally with the main body 31 to support the thin membranes 32A and 32B.

The higher fatty acids in reservoir 1 are introduced into channels 33X and 33Z of reaction unit 3 through inlets 34X and 34Z, respectively, by means of pump 2, while at the same time the lipase-containing glycerol of reservoir 9 is introduced into channel 33Y of reaction unit 3 through inlet 34 by means of pump 10. The thus-introduced feedstocks react upon contact through porous thin membranes 32A and 32B while being maintained at a predetermined reaction temperature by means of thermostatic bath 4. The reaction product, i.e., fatty acid glyceride, which is hydrophobic, moves into channels 33X and 33Z and is sent to reservoir 5 through outlets 35X and 35Z.

The water by-product intermingles with the lipase-containing glycerol and passes through channel 33Y, and then is sent through outlet 35Y to reservoir 6 where it is taken out of the system under reduced pressure by means of vacuum pump 7 while being well stirred. The water can also be taken out of the system by passing it through a column filled with a molecular sieve in place of using vacuum pump 7. The lipase-containing glycerol which has been dehydrated by the above-described procedure is returned to reservoir 9 and is again supplied to reaction unit 3.

In the above-described apparatus, the hydrophobic higher fatty acid and the solution or dispersion of hydrophilic glycerol and lipase can be introduced separately into the channels formed inside the main body and reacted upon contact with each other through the porous thin membrane. Furthermore, the hydrophobic fatty acid glyceride formed, the lipase-containing glycerol and water can be separated and recovered through the respective channels.

The structure of reaction unit 3 can be modified in various ways. Specifically, reaction unit 3 can have the cross-section structures as shown in FIGS. 3(A) to 3(D). In FIGS. 3(A) to 3(D), the reference numeral 310 represents the main body of the unit; 320 (320A, 320B, 320C, 320D) represents porous thin membranes; and 330 (330V, 330W, 330X, 330Y, 330Z) represents channels defined in the main body by the thin membranes 320 (320A, 320B, 320C, 320D). That is, the main body of the unit may be rectangular or circular in cross-section. In addition, the main body can take various forms such as a thin plate, a multilayer form, a spiral form, or a snaking form. Further, the porous thin membrane 320 may be plate-formed or cylindrical. Moreover, depending on the shape of the main body of the unit, the porous thin membrane 320 can be shaped in any desired form such as a spiral form, a tubular form or a hollow fiber form. The number of thin membranes is not critical and can be determined appropriately. The shape, size and number of channel 330 can change depending on the above-described main body and thin membrane employed.

In each structure of reaction unit 3, as the contact area between the two substrates which are introduced into the channels separately is increased, the contact time can be shortened. The shape and size of the main unit, and the size and number of the porous thin membranes can be determined appropriately taking into account, for example, the types of two substrates to be reacted, the type of enzyme to be used as a catalyst, the desired conversion, and the reaction temperature.

The inlet and outlet for each of the feedstock and reaction product can be provided so that the two substrates come into contact with each other countercurrently; that is, the two substrates may be introduced countercurrently.

As described above, the process and apparatus of the present invention produces various advantages. Some of the major advantages are detailed below.

(1) The lipase dissolved or dispersed in a hydrophilic substrate does not mix with either the hydrophobic substrate or the hydrophobic reaction product. Thus, the mixture of the hydrophilic substrate (water in the case of hydrolysis, and polyhydric alcohol in the case of esterification) and lipase can be recycled.

(2) Since a feedstock is introduced into the main body of the apparatus through an inlet and the product is withdrawn through an outlet, the reaction can be carried out continuously.

(3) Since the temperature is relatively low, i.e. in the neighborhood of room temperature, and the reaction is performed in an air-tight condition, a substrate of low oxidation stability (e.g. a substrate containing highly unsaturated fatty acids) is not subject to autoxidation isomerization of double bond, or positional migration.

(4) Expensive enzyme-immobilization is not needed.

(5) The hydrophilic substrate and the hydrophilic reaction product do not mix with the hydrophobic reaction product. Thus, no purification procedure is needed to remove impurities from the hydrophobic reaction product.

The present invention is described in greater detail with reference to the following non-limiting examples. In each example, the reaction apparatus and reaction conditions as described hereinafter were used and the type of thin membrane and the reaction temperature were varied.

REACTION APPARATUS

A thin main body, rectangular in cross-section, was provided with two porous thin membranes in parallel relation to each other to define therein three compartments, a top channel, a middle channel and a bottom channel. Each channel was provided with an inlet at one end thereof and an outlet at the other end.

The distance between the thin membranes was 350 $\mu$m; the distance between the main body and the thin membrane was 300 $\mu$m; the size of the thin membrane was 32 cm $\times$ 12 cm; and the effective contact area between the two substrates through the thin membrane (the area excluding those covered for attachment of the thin membrane) was 363 cm$^2$.

The apparatus was placed in a thermostatic bath so that the temperature could be controlled.

REACTION CONDITIONS

A hydrophobic substrate was passed through the top and bottom channels, and a hydrophilic substrate was passed through the middle channel. The flow rate was 14 ml/hour for each substrate.

EXAMPLE 1

A thin membrane made of polypropylene and having an average pore diameter of 2 $\mu$m, a porosity of 44%, and a thickness of 25 $\mu$m was used. The reaction temperature was adjusted to 40° C.

Olive oil (acid value, 0.2; saponification value, 189.9) was used as the hydrophobic substrate. A powder of lipase produced by *Candida cylindracea* was dissolved in water, a hydrophilic substrate, to prepare a 1,000 unit/ml aqueous solution. The olive oil and the aqueous solution flowed in the same direction and were brought into contact with each other through the thin membrane, whereupon the hydrolysis of the olive oil was achieved and there was obtained a hydrolyzate (acid value, 189.2; saponification value, 199.0).

The hydrolysis rate, determined by the equation described below, was 95.1%.

$$\text{Hydrolysis rate (\%)} = \frac{\text{Acid value}}{\text{Saponification value}} \times 100$$

EXAMPLE 2

In this example, a thin membrane made of polytetrafluoro ethylene having an average pore diameter of 0.7 $\mu$m, a porosity of 55% and a thickness of 50 $\mu$m was used, and the reaction temperature was adjusted to 55° C. As the lipase, a 950 unit/ml broth produced by *Chromobacterium viscosum* was used.

Tallow oil (acid value, 1.5; saponification value, 194.8) was hydrolyzed in the same manner as in Example 1, whereupon there was obtained a hydrolyzate (acid value, 173.0; saponification value, 201.6). The hydrolysis rate was 85.8%.

EXAMPLE 3

In this example, a thin membrane made of cellulose acetate having an average pore diameter of 0.5 $\mu$m, a porosity of 47% and a thickness of 25 $\mu$m was used. A powder of lipase produced by *Mucor miehei* was dissolved in water to prepare a 1,000 unit/ml aqueous solution.

Using the above-described aqueous solution, marine oil (acid value, 2.1; saponification value, 192.1) was hydrolyzed in the same manner as in Example 1. The hydrolysis rate of the hydrolyzate (acid value, 173.0; saponification value, 201.6) was 85.8%.

EXAMPLE 4

In this example, an esterification reaction was carried out at 40° C. using the same thin membrane as used in Example 3. As the hydrophobic substrate, docosahexaenoic acid (acid value, 167.7; saponification value, 168.9) was used, and a 1,000 unit/ml solution of lipase in ethylene glycol (purity, 98%), said lipase being produced by *Geotrichum candidum*, was used as the hydrophilic substrate.

The reaction product, i.e., hydrophobic ester, had an acid value of 22.6 and a saponification value of 157.3. The esterification rate of docosahexaenoic acid into ethylene glycol ester, as determined by the equation described below, was 85.6%.

$$\text{Esterification rate} = 1 - \frac{\text{Acid value}}{\text{Saponification value}} \times 100$$

EXAMPLE 5

In this example, an esterification reaction was carried out at 40° C. using the same thin membrane as used in Example 1. As the hydrophobic substrate, linoleic acid (acid value, 199.0; saponification value, 201.1) was used, and a 1,000 unit/ml solution of lipase in glycerol (purity, 95%), said lipase being produced by *Mucor miehei*, was used as the hydrophilic substrate.

The reaction product had an acid value of 10.6 and a saponification value of 192.4. The esterification rate of linoleic acid into glycerol ester was 94.5%.

EXAMPLE 6

In this example, an esterification reaction was carried out at 40° C. using the same thin membrane as used in Example 2. As the hydrophobic substrate, lauric acid was used, and a 900 unit/ml solution of lipase in propylene glycol (purity, 95%), said lipase being produced by *Geotrichum candidum*, was used as the hydrophilic substrate.

The reaction product had an acid value of 22.5 and a saponification value of 250.1. The esterification rate of lauric acid into propylene glycol ester was 91.0%.

While the invention has been described in detail and with reference to specific embodiments thereof, it will be apparent that changes and modifications can be made to the invention without departing from the spirit and scope thereof.

We claim:

1. A biochemical process comprising reacting a (a) hydrophobic substrate with (b) a solution or dispersion comprising a hydrophilic substrate and an enzyme catalyst, wherein said reacting is carried out by contacting said hydrophilic substrate and said hydrophobic substrate, which are separated by a porous thin membrane and do not intermingle, through the micropores of said porous thin membrane, wherein said porous thin membrane has a pore size of about 0.05 to 10 μm and a thickness of about 10 to 100 μm, and wherein said hydrophilic substrate and said hydrophobic substrate are incompatible with each other.

2. The process as claimed in claim 1, wherein the hydrophobic substrate is a fatty acid ester, the hydrophilic substrate is water, and the enzyme is lipase.

3. The process as claimed in claim 1, wherein the hydrophobic substrate is a fatty acid having 6 to 24 carbon atoms, the hydrophilic substrate is a polyhydric alcohol, and the enzyme is lipase.

4. The process as claimed in claims 2 or 3, wherein said lipase is derived from a microorganism, an animal organ or a plant seed.

5. The process of claim 4, wherein said microorganism is selected from the group consisting of Candida, Chromobacterium, Aspergillus, Penicillium, Mucor, Geotrichum, Rhizopus, and Arthrobacter.

6. The process of claim 1, wherein said porous thin membrane has a thickness of about 20 to 50 μm.

7. The process of claim 1, wherein said porous thin membrane has a porosity of about 20 to 80%.

8. The process of claim 1, wherein said porous thin membrane has a porosity of about 40 to 60%.

* * * * *